United States Patent [19]

Gainer

[11] 3,965,261

[45] June 22, 1976

[54] METHOD FOR TREATING PAPILLOMAS

[75] Inventor: John L. Gainer, Charlottesville, Va.

[73] Assignee: University of Virginia, Charlottesville, Va.

[22] Filed: Apr. 29, 1975

[21] Appl. No.: 572,631

[52] U.S. Cl. ............................................. 424/180
[51] Int. Cl.² .......................................... A61K 31/70
[58] Field of Search .................................. 424/180

[56] References Cited
UNITED STATES PATENTS
3,853,993   12/1974   Gainer ............................. 424/180

Primary Examiner—Jerome D. Goldberg
Attorney, Agent, or Firm—Oblon, Fisher, Spivak, McClelland & Maier

[57] ABSTRACT

A method for the treatment of Papillomas on a mammal which comprises administering to said mammal an effective dose of a water soluble carotenoid.

5 Claims, No Drawings

METHOD FOR TREATING PAPILLOMAS

BACKGROUND OF THE INVENTION

1. Field of the Invention

This invention relates to a novel technique for the treatment of Papillomas on mammals.

2. Description of the Prior Art

In applicant's prior applications, now U.S. Pat. Nos. 3,853,992 and 3,788,468, applicant disclosed that certain water-soluble carotenoids had been observed to possess quite unique properties. In particular, these water-soluble carotenoids have been found to increase the diffusivity of oxygen through aqueous media. Applicant theorized that this phenomenon might be applied to effect desirable biological effects. In particular, applicant theorized that if oxygen diffusivity in aqueous media could be enhanced, that this effect could be applied to increase the diffusivity of oxygen in blood. Applicant theorized further that by increasing the diffusivity of oxygen in the blood, atherosclerosis, which has long been theorized to be a disease resulting from local hypoxia of the vascular walls, could be successfully treated. This theory was applied to certain test animals, and, to the satisfaction of the inventors, the theory was proven to be correct, and in fact, a seemingly successful treatment of atherosclerosis was obtained.

Applicant has now continued to study the biological properties of this most unusual class of compounds, with the result that a new biological property has been discovered which is the subject matter of this application.

SUMMARY OF THE INVENTION

It has now been found that the water-soluble carotenoid compounds, such as crocetin and crocin, can be used effectively for the treatment and prevention of the formation of Papillomas.

DETAILED DESCRIPTION OF THE PREFERRED EMBODIMENTS

Pappillomas is a branching or lobulated benign tumor derived from epithelium. One theory of why this type of tumor develops is that a change occurs in the normal cells, a process called dedifferentiation due to the lack of oxygen in the tissues.

A wide variety of Papilloma can be treated by the methods of this invention, such as Papilloma diffusum, hard or soft Papilloma, intracanalicular Papilloma, intracystic Papilloma, or the like.

The carotenoids useful for this purpose are those of the form:

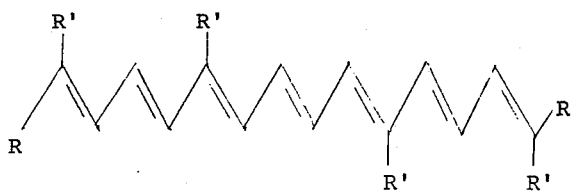

wherein each R may represent a hydrophilic group and each R' represents hydrogen or methyl. Suitable hydrophilic groups include the carboxyl groups or the ester groups of the form COOR'' wherein R'' represents a soluble sugar group, such as $C_{12}H_{21}O_{10}$, an alkanol group such as -CH$_2$-OH, -CH$_2$-CH$_2$-OH, or -CH$_2$-CH$_2$-CH$_2$-OH, or a carboxy substituted lower alkyl, such as -CH$_2$-COOH, -CH$_2$-CH$_2$COOH or -CH$_2$-CH$_2$-CH$_2$COOH, or each R and R' may represent a lower alkanol group, such as -CH$_2$-OH, -CH$_2$-CH$_2$-OH, or -CH$_2$-CH$_2$-CH$_2$-OH, a hydroxy group, or an amine group of the form -NH or NR''' wherein R''' is a lower alkyl, lower alkanol or carboyx substituted lower alkyl, or a carboxy substituted lower alkyl, such as -CH$_2$-CH$_2$-OH, -CH$_2$-OH, or -CH$_2$-CH$_2$-CH$_2$-OH.

Most preferred are crocetin, also known as 8,8'-diapo-8,8'-carotenoic acid, or crocin, also known as digentiobiosyl 8,8'-diapo-8,8'-carotenedioate.

The water soluble carotenoids have been found to be effective in the treatment and prevention of Papillomas when applied by either injection into the animal, or when applied topically directly onto the Papillomas, or onto the site of Papilloma susceptibility. The carotenoid can be applied topically in the form of an ointment, gel or liquid. In ointment form, it can be combined with any suitable pharmaceutical ointment carrier which is non-reactive with the active ingredient.

To prepare a gel form, any conventional gels can be used such as dextran, silica gel, or gum tragacanth. To prepare a liquid form, the carotenoid can be dissolved in water or in a hydrophilic solvent such as ethanol, isopropanol, acetone, glycol or the like. A highly volatile solvent is most preferred, since the solvent would tend to evaporate from the skin leaving the carotenoid in direct contact with the Papilloma.

The carotenoid can be injected into the patient, and in an injectable form, it may be combined with vitamins, choline, glycerophosphoric acid, glycol, glycerine or gum tragacanth, etc.

The animal or human is treated with from 0.001 to 1000 mg of active ingredient per kg of body weight each application, for a total weekly dose rate of 0.001 to 1000 mg of active ingredient per kg of body weight/day, and preferably, from 0.005 to 1000 mg/kg/week.

It is not clear that the effect of the carotenoids on Papilloma is a result of the oxygen diffusivity enhancing effect of the carotenoid. While one theory as to the cause of Papilloma is that there is some relationship between oxygen deficiency and dedifferentiation, the accuracy of this theory is only speculation. Moreover, there could be no prior assurance that the carotenoids could function to enhance oxygen diffusivity in tissue, which would be required to treat Papilloma.

The effectiveness of the water soluble carotenoids has been indicated by tests with Swiss-Webster mice, which are the standard test animals often used for experimental treatment techniques of non-malignant tumors, such as Papilloma.

In the testing of the pharmaceutical for efficacy, over 100 mice were tested. Papilloma was induced into the mice, and the mice were injected subcutaneously in the dorsal region, just below the neck.

Although the carotenoids have been identified herein as "water soluble carotenoids," it should be understood that they also are soluble in hydrocarbons due to their long chain hydrocarbon structure.

Having generally described the invention, a more complete understanding can be obtained by reference to certain specific examples, which are included for purposes of illustration only and are not intended to be limiting unless otherwise specified.

EXAMPLE 1

Male, Swiss-Webster mice, weighing about 25 grams each were treated with 7,12-dimethylbenz[α]anthracene on day 1 and day 15 of the test period by applying 0.2 ml of a 0.8 mg/ml solution in acetone to a 4 cm$^2$ area of skin on the backs of the mice. A solution of croton oil (4 mg/ml) in acetone was applied to the exposed skin every other day after day 15, 0.2 ml per mouse. 7,12-dimethylbenz[α]anthracene is a known chemical carcinogen, and croton oil is a skin irritant. This is a standard test procedure. Ten mice served as the control group and ten mice became the experimental group and were also given daily injections of 0.6 ml of isotonic saline containing approximately 30 mg/ml of the carotenoid compound, crocetin. The results were as follows:

| Time of Experiment (days) | Average Control | Papillomas per Mouse Crocetin-treated |
|---|---|---|
| 0 | 0 | 0 |
| 39 | 6.2 | 1.5 |
| 46 | 11.0 | 4.4 |
| 50 | 13.3 | 6.1 |
| 63 | 10.4 | 6.4 |
| 67 | 11.1 | 6.1 |

EXAMPLE 2

The tests of Example 1 were repeated except that the crocetin was applied topically instead of being injected. This time, the crocetin was dissolved in acetone at a concentration of about 100μ g/ml. The results were as follows:

| Time of Experiment (days) | Average Control | Papillomas per Mouse Crocetin-treated |
|---|---|---|
| 0 | 0 | 0 |
| 30 | 3.2 | 0.15 |
| 40 | 5.6 | 0.58 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method for the treatment of Papillomas on a mammal which comprises administering to a mammal in need of said treatment an anti-Papilloma effective amount of a water soluble carotenoid.

2. The method of claim 1, wherein said water soluble carotenoid has the formula

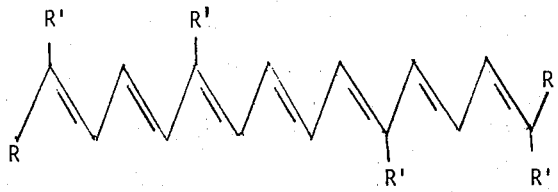

wherein each R is a hydrophilic group, and wherein each R' is hydrogen or methyl.

3. The method of claim 1, wherein said water-soluble carotenoid is crocin.

4. The method of claim 1, wherein said water-soluble carotenoid is crocetin.

5. The method of claim 1, wherein said water-soluble carotenoid is administered intraveneously or topically at a dose rate of from 0.001 mg to 1000 mg active ingredient per kg of body weight per week.

* * * * *